US010603407B2

(12) United States Patent
Selim et al.

(10) Patent No.: US 10,603,407 B2
(45) Date of Patent: *Mar. 31, 2020

(54) COLLAGEN MATRIX FOR CELL THERAPY

(71) Applicant: Warsaw Orthopedic, Inc., Warsaw, IN (US)

(72) Inventors: Abdulhafez A. Selim, Cliffwood, NJ (US); Lawrence A. Shimp, Morganville, NJ (US); Hsiu Ying Sherry Wang, North Brunswick, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 374 days.

This patent is subject to a terminal disclaimer.

(21) Appl. No.: 15/388,936

(22) Filed: Dec. 22, 2016

(65) Prior Publication Data
US 2017/0100511 A1 Apr. 13, 2017

Related U.S. Application Data

(62) Division of application No. 13/096,656, filed on Apr. 28, 2011, now Pat. No. 9,540,610.

(51) Int. Cl.
| | |
|---|---|
| *A61K 35/28* | (2015.01) |
| *A61L 27/24* | (2006.01) |
| *A61K 9/00* | (2006.01) |
| *A61K 9/06* | (2006.01) |
| *A61K 38/39* | (2006.01) |
| *C12N 5/00* | (2006.01) |
| *A61L 27/38* | (2006.01) |
| *A61L 27/48* | (2006.01) |

(52) U.S. Cl.
CPC ............ *A61L 27/24* (2013.01); *A61K 9/0024* (2013.01); *A61K 9/06* (2013.01); *A61K 35/28* (2013.01); *A61K 38/39* (2013.01); *A61L 27/3804* (2013.01); *A61L 27/3817* (2013.01); *A61L 27/3821* (2013.01); *A61L 27/3895* (2013.01); *A61L 27/48* (2013.01); *C12N 5/0068* (2013.01); *A61L 2400/06* (2013.01); *A61L 2430/06* (2013.01); *C12N 2533/54* (2013.01); *C12N 2533/90* (2013.01); *C12N 2533/92* (2013.01)

(58) Field of Classification Search
None
See application file for complete search history.

(56) References Cited

U.S. PATENT DOCUMENTS

| | | | |
|---|---|---|---|
| 5,219,895 A | 6/1993 | Kelman et al. | |
| 5,374,539 A | 12/1994 | Nimni et al. | 435/68.1 |
| 6,455,309 B2 | 9/2002 | Stone | |
| 2003/0133967 A1 | 7/2003 | Ruszczak et al. | 424/443 |
| 2006/0073592 A1 | 4/2006 | Sun et al. | 435/423 |
| 2007/0190108 A1* | 8/2007 | Datta | A61L 27/48 424/423 |
| 2009/0157193 A1 | 6/2009 | McKay | |
| 2009/0312524 A1 | 12/2009 | Lauritzen | |

FOREIGN PATENT DOCUMENTS

| | | |
|---|---|---|
| WO | 9011092 A1 | 10/1990 |
| WO | WO02002024244 | 3/2002 |
| WO | WO 2009009620 | 1/2009 |

OTHER PUBLICATIONS

Zhu et al, (Current Drug Targets, 6: 97-110, 2005) (Year: 2005).*
Skop et al (Molecular and Cellular Therapies, 2 (1(:1-15, 2014) (Year: 2014).*
Chen et al (Biomaterials, 28: 1027-1035, 2007).

* cited by examiner

*Primary Examiner* — Anoop K Singh
*Assistant Examiner* — Magdalene K Sgagias

(57) ABSTRACT

The invention relates to the use of an active collagen matrix for culturing mammalian cells and the use of the active collagen matrix and cells for the treatment of disease.

4 Claims, 4 Drawing Sheets

COLLAGEN MATRIX FOR CELL THERAPY

CROSS-REFERENCE TO RELATED APPLICATIONS

This application is a divisional application of U.S. patent application Ser. No. 13/096,656 filed on Apr. 28, 2011, entitled "COLLAGEN MATRIX FOR CELL THERAPY" which is related to and was filed concurrently with U.S. application Ser. No. 13/096,570, entitled "SOFT TISSUE WRAP", and U.S. application Ser. No. 13/096,630, entitled "COLLAGEN MATRIX FOR TISSUE ENGINEERING", the entirety of each of which is incorporated herein by reference.

FIELD OF THE INVENTION

The invention relates generally to a method for using a mammalian-derived active collagen matrix to support the grown of cells, and to cell culture vessels using the active collagen matrix.

BACKGROUND

Stem cells can be proliferated or expanded and differentiated into many different cell types, primarily depending upon the type and source of the initial stem cell. Stem cells are of high interest to the research community and regenerative industry because of these features. In particular the ability to expand the population and direct differentiation has led to intense study of stem cells for the purpose of supplying cells and tissues to cure human diseases.

Human pluripotent stem cells are currently being proliferated and directed to differentiate into specific lineages, particularly for the development of therapeutic objectives. In addition, they are very useful scientific tools for the study of cellular processes and differentiation.

Basic techniques for culturing human cells have been described, but there are limitations and drawbacks to many of the procedures currently used. For example, mouse embryonic fibroblast feeder cells have been used to culture human ES cells. Likewise, conditioned medium using bovine collagen as a base layer has been used to grow stem cells. However, the growth of stem cells on non-human feeder cells and the use of conditioned media raise concerns that one or more agents, such as a virus, could be introduced into the cells and subsequently transmitted to a patient.

Cells can be cultured on a collagen support, however if those cells are to be transplanted into a human subject that collagen support should be human collagen.

Collagen is used as an implant material to replace or augment hard or soft connective tissue, such as skin, tendons, cartilage, and bone. Some implants are formed as solid, flexible, or deformable collagen masses cross-linked with chemical agents, radiation, or other means to improve mechanical properties, decrease the chance of an immunogenic response, and/or to manage the resorption rate, or to improve the mechanical properties.

Collagen-based medical implants for use in humans generally have been of a non-human origin, i.e., xenogenic. A problem with the use of xenogenic tissue as a starting material when generating medical implants is that the tissue may be contaminated with viruses or prions. For example, products using bovine sourced tissue have the potential for transmitting BSE (Bovine Spongiform Encephalopathy).

Another problem with the use of xenogenic tissue is the potential for inflammation responses, hematomas, adhesions, and rejection after implantation. This is because xenogenic collagen and telopeptides can include antigens and other constituents that can initiate an immunogenic response in humans. Additionally, a certain proportion of patients can develop allergic reactions to implanted xenogeneic materials.

Thus, there is a need for methods to isolate collagen fiber and/or thread base materials for products made from the collagen fiber and/or thread base materials that are less likely to produce an immunogenic response.

The inventor here has found an improved collagen composition that increases the growth rate of human cells. This provides both an improved matrix for growing cells and also allows the cells and matrix to be implanted into a mammalian subject.

SUMMARY OF THE INVENTION

The invention relates to a defined support substrate for culturing mammalian cells. The support substrate is animal product-free and increases the growth rate of cells relative to an animal based substrate.

Another aspect of the invention provides a method for culturing primate mesenchymal cells, mesenchymal stem cells or stem cells on an active collagen matrix with a defined medium without the need for feeder cells or conditioned medium. Another aspect of the invention provides a method for culturing primate mesenchymal cells, mesenchymal stem cells or stem cells on an active collagen matrix with a defined medium, such as Dulbecco's Modified Eagle Medium or the like, without the need for feeder cells or conditioned medium through multiple successive culture passages. The method includes the step of culturing cells in a medium including salts, vitamins, amino acids, glucose, lipids, and one or more growth factors, all in sufficient amount to maintain the cells.

In some exemplary embodiments, human active collagen matrix may be formed from collagen products having a preserved amount of native human constituents. Such collagen products may include collagen fiber, fibrillar collagen, microfibrillar collagen, particulate collagen, collagen thread, intermediate collagen products that may or may not contain alcohol, and that may or may not be derived from a foam containing collagen and a leveling agent.

In one exemplary embodiment, the active collagen matrix is obtained by blending a dispersion of human collagen product fiber and/or thread base materials and a volume between about 2% to about 15% of an alcohol having a purity of about 70% to about 99.999%; reconstituting a foam component of the blended collagen product dispersion into a liquid phase; and removing the liquid component of the reconstituted collagen product dispersion. Optionally, removing the liquid component from an intermediate collagen product allows the collagen to be formed as collagen films, collagen strands, fibers, filaments, threads and fabrics produced therefrom, collagen plugs, and collagen scaffolds, and combinations and variations thereof for use in culturing cells.

In another exemplary embodiment, the collagen fibers, films, strands, filaments, threads and fabrics, plugs and scaffolds are used to support in vitro cell culture, for example, culturing primate mesenchymal cells, mesenchymal stem cells or stem cells, without the need for feeder cells or conditioned medium.

In some embodiments, there is a collagen and conserved natural growth factors, wherein the collagen and conserved natural growth factors are derived from a human or recombinant animal source and the collagen is cross-linked and is in the form of a sheet that is at least 50% porous. A conserved growth factor is one that is associated with the collagen when the collagen is in its naturally occurring state, and it is also associated with the collagen by the same types of bonds after processing, and thus does not change form during processing. In another exemplary embodiment, the collagen fibrils may be modified by one or more enzymes that modify the collagen without disrupting the fibrils. In another exemplary embodiment, the collagen fibers may be further broken down, for example, the fiber may be broken down to fibrils, to make a suspension. In another exemplary embodiment, the fibrils or partially broken down collagen may be reassembled. This collagen that has conserved growth factors may also be referred to as "normal collagen" or "active collagen." In some embodiments the collagen support consists of human collagen, and in other embodiments, it may also or alternatively comprise collagen from a human compatible recombinant animal source that has conserved growth factors as well as animal collagen with enzymatically removed proteoglycan groups (by enzymes such as is described in U.S. Pat. No. 6,455,309 and related patents).

In some embodiments, the present application provides a method for making a soft tissue wrap comprising: subjecting human collagen (or collagen from a recombinant animal source or enzymatically modified animal source) to an acid suspension; exposing the human collagen to formaldehyde, gluteraldehyde, genipin or other cross-linking agent thereby causing the human collagen to cross-link; and forming a sheet from the human collagen; wherein the human collagen has not been exposed to any enzymes that are capable of removing or denaturing soft tissue growth factors that are associated with the human collagen. This processing technique allows the growth factors to be conserved.

In various embodiments, the present application may take advantage of the fact that human collagen is immune privileged in humans. The phrase "immune privileged" means that it will not induce an immunologically adverse response in the host into which it is introduced. Thus, in some embodiments, by avoiding enzyme treatments, high pH and oxidizing treatments, the naturally occurring proteins that are associated with collagen in its naturally occurring state may be conserved and the recipient organism will not mount an immunological response to the active collagen. This combination of factors can greatly facilitate healing and repair of soft tissue. In some embodiments, the collagen is not immunogenic.

Another aspect of the invention provides a kit for culturing human mesenchymal cells or stem cells on a human collagen matrix, comprising a collagen matrix attached to a surface of a cell culture flask. For example, the human collagen may be coated on the interior surface of a disposable cell culture flask that may be 12.5 $cm^2$, 25 $cm^2$, 75 $cm^2$, 150 $cm^2$, 175 $cm^2$, 225 $cm^2$, or 300 $cm^2$ in size. The culture flask may also include fibronectin, laminin and/or vitronectin. Optionally, one or more growth and/or differentiation factors may be added, typically this is accomplished by the addition of serum. In an exemplary embodiment, human serum is used at a concentration of 1% to 20% by volume.

In another exemplary embodiment, the invention provides a cell support system for use in an industrial reactor or fermentor.

In another exemplary embodiment, the invention provides a culture flask, primate cells (e.g., mesenchymal cells, mesenchymal stem cells or stem cells), and a human collagen based matrix on which the cells can grow. Optionally, a culture medium comprising salts, vitamins, amino acids, glucose, minerals, lipids, and one or more growth factors or proteins or other supplements, such as human serum, may also be supplied.

In an exemplary embodiment, the collagen matrix has a preserved amount of native human constituents. Such collagen products may include collagen fiber, fibrillar collagen, microfibrillar collagen, particulate collagen, collagen thread, intermediate collagen products that may or may not contain alcohol, and that may or may not be derived from a foam containing collagen and a leveling agent.

In another exemplary embodiment, the collagen matrix is prepared by blending a dispersion of human collagen fiber and/or thread base materials and a volume between about 2% to about 15% of an alcohol having a purity of about 70% to about 99.999%; reconstituting a foam component of the blended collagen product dispersion into a liquid phase; and removing the liquid component of the reconstituted collagen product dispersion. Removing the liquid component from the intermediate collagen product may be performed in a culture flask, thereby providing an adhesion surface in the culture vessel.

Another aspect of the invention provides a method for initiating a cultured line of primate stem cells without the use of feeder cells or conditioned medium, the method including the step of plating mesenchymal stem cells onto an active collagen matrix derived from a human tissue in a culture medium. Yet another aspect of the invention provides a method of repairing bone, by plating mesenchymal stem cells onto an active collagen matrix in culture media, culturing the cells to expand the population, optionally treating the cells to induce differentiation into osteoprogenitor cells, harvesting the cells and matrix, and implanting the matrix and cells in a subject suffering from a bone defect.

Another aspect of the invention provides a culture of human stem cells on a matrix of human collagen proteins that retain native growth factors.

Another aspect of the invention provides a method for providing engineered tissue, the method comprising culturing of human or animal cells, including, but not limited to, skin, muscle, cartilage, bone, marrow, endothelial and stem cells, to provide substitutes to replace damaged components in mammals, such as humans. The active collagen matrix may be used as a template that allows cells to grow (they may also differentiate) in three dimensions to form new tissues, where optionally the active collagen matrix is gradually absorbed and/or replaced with other extracellular material or cell-cell junctions.

The active collagen matrix, cell culture and/or engineered tissue may also comprise a polymer scaffold, for example, scaffolds made from polylactide, polyglycolide, polyglycolic acid, polylactide-co-glycolide, polylactic acid-polyethylene oxide copolymers, modified cellulose, polyhydroxpriopionic acid, polycaprolactone, polycarbonates, polyamides, glycosaminoglycan, hyaluronic acid, chondroitin, glucosamine and combinations thereof. The active collagen matrix, cell culture and/or engineered tissue may also comprise one or more aqueous gelling agents, including, but not limited to, various carbopol polymers, alginate, chitosan and combinations thereof, anti inflammatory agents, including, but not limited to, Omega-3 EFA, EPA, DHA, white willow bark, salicin, curcumin, epigallocatechin-3 galate, pycnogenol, olibanum, uncaria tomentosa, capsaicin, ginger, glucocorticoids, corticosteroids, mannose-6-phosphate, heparin, castanospermine, licofelone, NSAIDs, COX inhibitors, mannose, galactose, vitamin D and combinations thereof.

The cells used in combination with the active collagen matrix may be autologous cells or allogeneic cells.

Other features and advantages of the present invention will become apparent from the following specification.

DETAILED DESCRIPTION OF THE INVENTION

Figure 1:
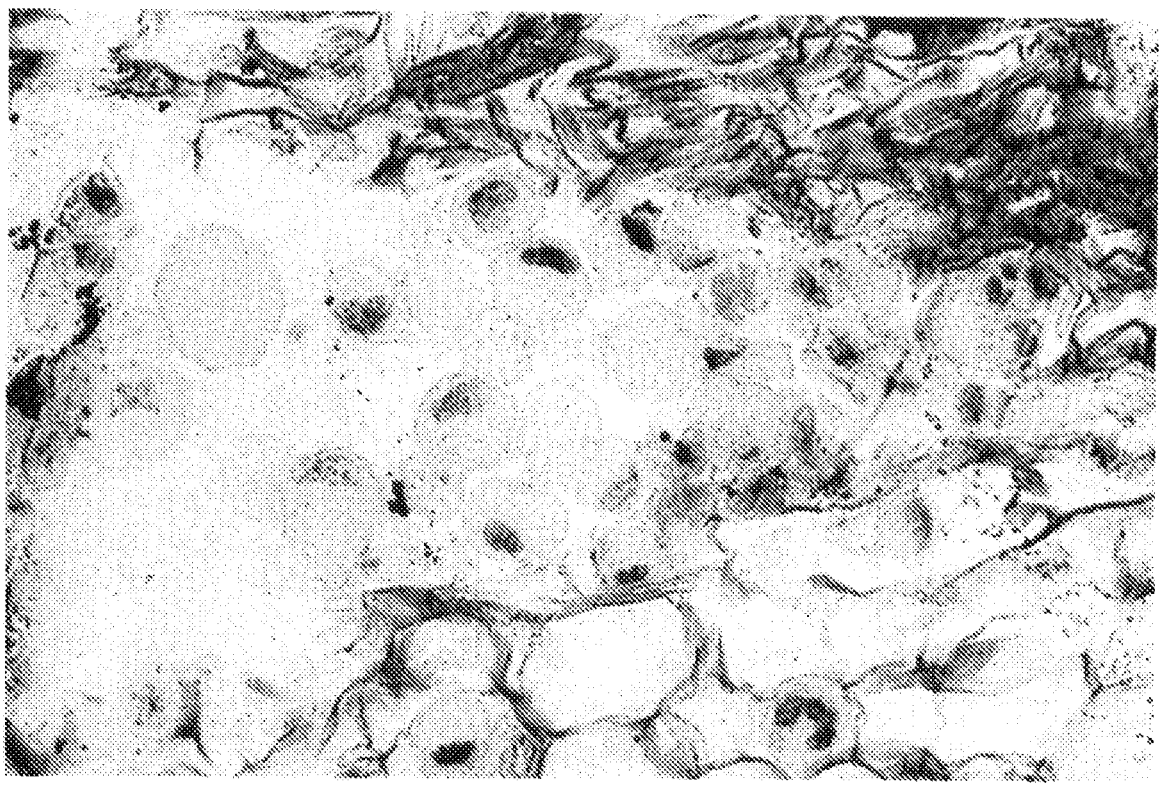
FIG. 1 shows human collagen membrane as a cell carrier for various applications. Mesenchymal cells were grown on human collagen membrane for 24 hours. Toluidine blue staining shows collagen fibers (dark blue) and cells (light blue with dark nuclei).

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

"Passage" is defined herein as the growth of stem cells from an initial seed culture to confluence in a culture vessel.

As used herein, "progenitor cell" means a cell that retains the ability to differentiate into a specific type of cell, but that cannot replicate indefinitely.

As used herein, "mammal" means any air-breathing, warm blooded, vertebrate animal air-breathing vertebrate animal where the mammary glands are functional in mothers with young, including, but not limited to humans, dogs, cats, horses and other mammals.

As used herein "active collagen matrix" means a collagen preparation prepared from a mammalian tissue that is essentially devoid of tissue cells and retaining native signaling proteins, such as growth factors, bone morphogenic proteins (BMPs), etc.

A method for preparing human-derived collagen from may include dehydrating a collagen suspension. In addition, the collagen may be compressed, before or after cross-linking, to reduce porosity, for example, the collagen may be compressed first and then subjected to cross-linking to render a collagen soft tissue wrap that retains lower porosity upon rehydration. Likewise, the collagen may be cross-linked in a higher porosity state and then compressed to yield a collagen matrix that will expand upon rehydration.

The growth factors include osteoinductive agents (e.g., agents that cause new bone growth in an area where there was none) and/or osteoconductive agents (e.g., agents that cause ingrowth of cells) and also fibrous or soft tissue inducing agents. Osteoinductive agents can be polypeptides or polynucleotide compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF) (this is specific for tendon/ligament), Osteoprotegerin, Growth Differentiation Factors (GDFs), Cartilage Derived Morphogenic Proteins (CDMPs, which can be a foundation for soft or hard tissue), Lim Mineralization Proteins (LMPs), Platelet derived growth factor, (PDGF or rhPDGF which is especially good for soft tissue), Insulin-like growth factor (IGF) or Transforming Growth Factor beta (TGF-beta) polynucleotides.

The active collagen matrix may also comprise one or more additional growth factors, including but not limited to rhBMP12, BMP7. These additional growth factors, unlike the conserved proteins are ones that have been added to the collagen during a subsequent processing step. The identity of proteins may be the same or different than the conserved proteins. In some embodiments the collagen may be treated so that it also binds to these additional proteins. In other embodiments, these additional proteins are not bound to the collagen, but are loosely associated with the collagen. In some embodiments, the resulting concentration of growth factors is from 10% to 30% greater than in the natural state or from 30% to 50% greater than in the natural state or from 50% to 70% greater than in the natural state.

In addition to including soft tissue factors that have the same identity as one or more of the conserved soft tissue growth factors noted above, the additional growth factors include polynucleotide compositions. Polynucleotide compositions include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, optionally the collagen matrix is treated with another activated collagen. The treatment may be carried out after cross-linking of the collagen within the collagen matrix. The additional activated collagen is collagen that is derived from a human or engineered animal to render it human compatible. This additional collagen may be activated by making it into a suspension without the use of an enzyme treatment or high pH, which would correspond to a strong base. The collagen suspension may then be applied to a collagen membrane by, for example, painting the suspension on the surface and letting it dry or using the collagen membrane as a filter and putting the liquid suspension of activated collagen through with a vacuum so that the liquid is removed and the suspension is trapped in the pores in the membrane.

In other embodiments, a suspension of activated collagen matrix, from whatever species of mammal, e.g., non-immunogenic human collagen fiber, includes a preserved amount of its native human constituents, e.g., native signaling factors and can be used in the invention. Collagen that contains a preserved amount of its native human constituents retains a sufficient or effective amount of the original collagen structure and/or constituents, including non-collagenous proteins and/or cross-link chemistries, to be suitable or therapeutically beneficial for the growth of cells derived from the same species and the original source tissue of the active collagen matrix.

In another exemplary embodiment, the invention provides an active collagen matrix by obtaining human collagen (or collagen from an engineered source to make it compatible with human collagen) and subjecting it to an acid suspension. The acid may be selected to degrade undesirable substances, while leaving intact the soft tissue growth factors.

The human collagen matrix may also be exposed to formaldehyde, or other cross-linking agents, causing the collagen to cross-link. In this method, preferably, the human collagen has not been exposed to any enzymes that are capable of removing soft tissue growth factors that are associated with the human collagen. Additionally, in some embodiments, it is not exposed to any alkali. Thus, the process allows the soft tissue growth factors to be conserved.

In some embodiments, the active collagen matrix is also exposed to human collagen that is not active. This active collagen matrix may have been subjected to conditions that remove certain proteins such as enzymes and/or alkali conditions.

Human fascia may be used as a starting material for preparing human collagen. Collagen fibers in fascia are extra-cellular protein units (e.g., helical assemblies) that are about 300,000 nanometers in length. Any human collagen source may be used including tendon, skin, bladder, small intestine submucosal tissue, etc.

Fibrillar collagen may be made from milled collagen fibers. A method for preparing human collagen, involves alkaline treatment, which may also include additional steps, e.g., treatment with a proteoglycan-depleting factor and/or glycosidase, or treatment with a mild enzyme that does not destroy all non-collagenous proteins in the harvested human collagen-containing tissue to separate collagen fiber and/or thread base materials from other components, while retaining certain native constituents and receptivity of the active collagen matrix. For example, native constituents may include uniquely human or biological characteristics, which allow the collagen to be biocompatible. In some implementations, the enzyme treatment breaks down some of the telopeptide bonds, while leaving others intact. This results in partly bound collagen fiber and/or thread base materials retaining a portion of the native non-collagenous proteins. The fiber and/or thread base materials are non-immunogenic in recipients of the same species. However, it will be understood that collagen products may be prepared using any known method.

The collagen matrix may be further processed to enzymatically remove proteoglycan groups (by enzymes such as is described in U.S. Pat. No. 6,455,309 and related patents), preserving the original or native constituents in an active collagen matrix, growth of mammalian, e.g., human cells, such as human stem cells, can be improved. An additional benefit is that the active collagen matrix and cells may be used as an implant in a human subject, particularly for the beneficial growth of bone, without triggering a significant immunogenic response.

In another exemplary embodiment, the active collagen matrix preparation method of the present invention does not use an alkali treatment step, and a non-alkaline solution is used for enzyme deactivation. This is useful according to embodiments of the present invention because certain collagen constituents native to mammals, such as humans, e.g., human growth factors and morphogenic proteins that would otherwise be stripped away by exposure to an alkaline solution, are maintained. In addition, because the collagen fibers are derived from the same mammalian species as the cells to be grown thereon, harsh purification and/or treatment processes may be unnecessary because the mammalian collagen tissue is less likely to be contaminated with detrimental contaminants or to illicit an immunological response to any residual material. It will be understood that the active collagen matrix may be produced using a variety of methods and may include collagen processing steps in addition to or as an alternative to the processing steps described herein.

The collagen can be optionally cross-linked. If it is cross-linked, a cross-linking agent that causes minimal damage to the proteins is preferred. Such cross-linking agents include, for example, genepin, and sugar based materials. Another approach is to add an active collagen suspension or particles to the cross linked matrix. The suspension is made without cross-linking and is precipitated on the cross-linked sponge surface by standard techniques such as raising the pH of the suspension. Alternatively, the suspension can be precipitated, dried, ground, resuspended and applied to the matrix.

In an exemplary embodiment, the active collagen matrix contains native growth factors from a mammalian source, such as a human or genetically engineered pig, and has been processed without damaging proteases enzyme treatments, or any other physical or chemical treatment that will remove or denature all of the native growth factors. The active collagen matrix may be obtained from any collagen containing organ or tissue source, such as skin, fascia, intestine, tendon, bladder, trachea, etc.

The isolated, enzyme treated, active collagen fibers of the invention include native collagen constituents and increase the growth rate of cells, such as human, cat, dog or horse stem cells. Current methods of culturing cells, including human stem cells, typically use bovine proteins as the attachment substrate. The present invention provides an improved growth substrate for the growth of mammalian cells, such as human stem cells, and also allows those cells to be collected along with the active collagen matrix, wherein the both the cells and collagen fibers (matrix) may be implanted into a subject to provide beneficial cellular responses and prevent an adverse reaction to the collagen matrix material. For example, human stem cells may be obtained from a human subject and expanded in combination with an active collagen matrix obtained from a human collagen tissue source and the expanded population and collagen matrix can be implanted back into the subject either in the form of a cell based therapy or the cells may be differentiated to produce a tissue that may then be used in the subject.

The active collagen matrix may be loaded into a culture flask to a depth ranging from any thickness greater than 0 mm to several inches thick, or about 0.5 mm to about 35 mm, or at a depth of about 4 mm. For example, some dispersion depths may include about 5, 7, or 12 mm. However, the depth the active collagen matrix loaded into a culture vessel is based on the desired thickness of the end product, which may be about 0.1 mm to about 15 cm in height, and may cover all of a surface in the culture vessel or a part of a surface in the culture vessel.

A culture media needs to provide the necessary nutrients, growth factors, and hormones for cell growth, and plays a role in regulating pH and osmotic pressure. Three basic classes of media can be used, basal media, reduced-serum media, and serum-free media. Serum is typically used as a source of growth and adhesion factors, hormones, lipids and minerals. In addition, factors in the serum also help regulate cell membrane permeability and it also serves as a carrier for lipids, enzymes, micronutrients, and trace elements. In an exemplary embodiment, the serum used to grow cells is a human serum, optionally, a human serum that has been tested for quality, safety, consistency, and regulatory compliance. In another exemplary embodiment, the serum source, active collagen matrix and cells are all from the same mammalian species. In yet another exemplary embodiment, the serum source, active collagen matrix and cells are all from the same organism.

In another exemplary embodiment, serum-free media is used. For example, an input population of progenitor or stem cells may be cultured in a liquid nutrient medium that is essentially free of serum as a supplement, but that does contain the components essential for survival and expansion of the particular cell line, for example, mesenchymal progenitor cells. A variety of liquid nutrient media, such as basal nutrient media, are suitable for use as a starting material, to which is then added the appropriate growth factors, nutrients and/or osmotic regulators necessary.

In another embodiment, the cells are cultured under non-static, adherent, conditions in the presence of chemically defined media available commercially for the culturing of human cells, e.g., human progenitor cells, including the StemSpan™ Serum-Free Expansion medium available commercially from StemCell Technologies in Vancouver, British Columbia. Alternatively, the culturing medium can be Dulbecco's Modified Eagle's Medium (DMEM), Iscove's Modified Dulbecco's Medium, McCoy's Modified 5A Medium, Minimum Essential Medium Eagle, RPMI 1640 Medium, Ham's F12 and mixtures thereof, for instance as described in U.S. Pat. No. 6,617,161. In another embodiment, the media in which the cells are cultured is supplemented with one or more growth factors, or cellular sources thereof, which enhance survival and expansion of human cells, such as human mesenchymal stem cells and human embryonic stem cells.

The culture media may be supplemented with stem cell factor (SCF), fibroblast growth factor (FGF), platelet derived growth factor (PDGF), cytokines, gamma-aminobutyric acid (GABA), pipecolic acid (PA), lithium chloride (LiCl), transforming growth factor beta (TGFβ) and/or interleukin-3 (IL-3). In an exemplary embodiment, mesenchymal progenitor cells are cultured on the human collagen matrix with at least SCF and IL-3 added to the culture media. When incorporated in the culture medium for mesenchymal stem cells, SCF and IL-3 may be present at concentrations of about 1-100 ng/mL for IL-3 and about 10-1,000 ng/mL for SCF.

Cell culture temperatures are typically grown at or near physiological temperature, about 37° C., with an appropriate blend of $O_2$ and $CO_2$, e.g., humidified 5% $CO_2$ in air.

The cells that can be beneficially used with a human active collagen matrix include any human cells, including stem cells that can in turn give rise to a wide variety of cell types and tissues of therapeutic interest, including nerve tissue, connective tissue, muscle, tendon/ligament, bone, cartilage, adipose tissue and/or vascular endothelium. For example, mesenchymal stem cells may be used, which in turn can differentiate into osteocytes, chondrocytes, adipocytes and other mesenchymal cell types. Differentiated mesenchymal stem cells may be used to grow or repair such tissues as bone, cartilage, muscle (including cardiac tissue), tendon and adipose. In an exemplary embodiment the mesenchymal cells are CD45−. In another exemplary embodiment the mesenchymal cells are CD45−/CD123+. In another exemplary embodiment, the stem cells may be pluripotent stem cells isolated from umbilical cord blood, e.g., CD45-negative unrestricted somatic stem cells.

In another exemplary embodiment, the cell population is derived or obtained from bone marrow stroma, umbilical cord, umbilical cord blood and/or peripheral blood.

In another exemplary embodiment, the active collagen matrix is processed to yield small beads that may then be suspended in a culture media and the cells cultured without attachment to a vessel surface. In another exemplary embodiment, the active collagen matrix may comprise particles having a size from about 25 microns to about 75 microns.

When cultured in vitro under conditions that promote differentiation to a osteoblast like phenotype, mesenchymal stem cells and/or osteoblast progenitor cells proliferate to form colonies of cells that express alkaline phosphatase and ultimately yield a mature osteoblast phenotype. These cells, along with the active collagen matrix, may be used to provide a primarily cell based treatment or the cells may be grown out in three dimensions and differentiated so as to form a tissue. Active collagen derived from various tissues may be used to support different types of tissue engineering. For example, collagen derived from soft tissues, such as muscle, bladder, etc., may be used to support the generation of new tissue of the same type. In particular, an active collagen matrix derived from a tendon may be used to grow and optionally differentiate, stem cells that may then be used to provide a stem cell therapy for regeneration of a tendon or engineering the growth of a tendon. In this embodiment, the activated collagen matrix may be obtained from an appropriate origin tissue, such as a tendon, and retains the appropriate growth factors and differentiation signals necessary to signal cellular differentiation to facilitate differentiation of cells into appropriate lineages for the origin tissue.

For differentiation into osteoblasts, the stem cells may be plated at the appropriate cell density in combination with the active collagen matrix and at the desired confluence the cells may be supplemented with the appropriate growth factors, for example, dexamethasone, ascorbic acid-2 phosphate, and/or β-glycerol phosphate. For chondrogenic differentiation, the stem cells may be cultured in DMEM high glucose, optionally supplemented with antibiotic, and the appropriate growth factors, for example, dexamethasone, ascorbic acid-2-phosphate, sodium pyruvate and/or TGFβ1. See also: D. Baksh, L. Song and R. S. Tuan, Adult Mesenchymal Stem Cells: Characterization, Differentiation, and Application in Cell and Gene Therapy, *J. Cell. Mol. Med.* Vol 8, No 3, 2004, pp. 301-316; N. zur Nieden, Embryonic Stem Cell Therapy For Osteo-Degenerative Diseases, *BioTechnologyI* April/May 2005; Naomi Ogura, Masaru Kawada, Wei-Jen Chang, Qi Zhang, Sheng-Yang Lee, Toshirou Kondoh and Yoshimitsu Abiko, Differentiation Of The Human Mesenchymal Stem Cells Derived From Bone Marrow And Enhancement Of Cell Attachment By Fibronectin, *J. Oral Science*, Vol. 46, No. 4, pp. 207-213, 2004; and Michael S. Friedman, Michael W. Long and Kurt D. Hankenson, Osteogenic Differentiation of Human Mesenchymal Stem Cells Is Regulated by Bone Morphogenetic Protein-6, *J. Cellular Biochemistry* 98:538-554 (2006).

In an exemplary embodiment, the invention provides a methodology for the treatment of joint disease and related cartilage damage. For example, cartilage may be grown in contact with the active collagen matrix and used to restore or regenerate cartilage in a subject, thereby providing a treatment for symptomatic joint pain. Likewise, tendon or ligaments may be formed in combination with the active collagen matrix and used to repair, replace or regenerate damaged tendons and ligaments. Optionally, one or more carrier components, adjuvants and/or pharmaceutical agents may be used or added to the cells and active collagen matrix.

Human cell lines that may be beneficially grown on a human active collagen matrix include, but are not limited to, human ES cell lines H1, H7, H9 and H14. In another embodiment, adult mesenchymal stem cells may be isolated from bone marrow, e.g., bone marrow aspirate, and can be expanded in culture, either while maintaining their pluripotency or by inducing differentiation into a desired lineage. When human cells are grown on a human active collagen matrix according to the invention the cells and matrix may be used for tissue engineering of bone, cartilage, fat, marrow stroma, muscle, tendon, and other mesenchymal derived tissues. For example, mesenchymal stem cells may be differentiated using appropriate growth factors into such cell types as osteoblasts, chondrocytes, myocytes, adipocytes, cardiomyocytes and neurons.

In another exemplary embodiment, the active collagen matrix may be supplemented with one or more growth factors, recombinant proteins, synthetic peptides, anti-inflammatory agents, antibiotics, anti-cancer agents, analgesics, anti-coagulants, etc.

The invention will now be more particularly described with reference to the following specific examples. It will be understood that these examples are illustrative and not limiting of the embodiments of the invention.

Example 1

The concentration of growth factors per gram of bovine subintestinal serosa (SIS) collagen membrane was analyzed. This membrane is a suspended and reformed collagen made into a sheet. No fgicin (or other enzyme) was used nor was any cross-linking agent used. One gram of SIS membrane was digested with crude bacterial collagenase (2 mg/ml) for 2 hours at 37° C. Digested material was centrifuged at 4000 rpm at room temperature for 15 minutes. Supernatant was filtered and used for ELISA assays (R&D systems).

TABLE 1

| Growth Factor | Concentration |
| --- | --- |
| PDGF | non-detectable |
| TGF alpha | non-detectable |
| FGF basic | 12064 pg/gram |
| BMP2 | 1.695 pg/gram |

Example 2

Cells in FIG. 1 are demonstrating an enhanced proliferation rate on human collagen membranes compared to bovine collagen membranes. Mesenchymal cells were grown on human collagen membrane for 24 hours and stained with Toluidine blue, which shows collagen fibers (dark staining) and cells (light staining with dark nuclei). This illustrates the advantageous use of human collagen membrane as a cell carrier for various cellular applications, such as cell culture. In addition, the beneficial growth also yields the option to use both the culture adhesion surface and an increased number of cells to produce a medical implant.

Example 3

Figure 2:
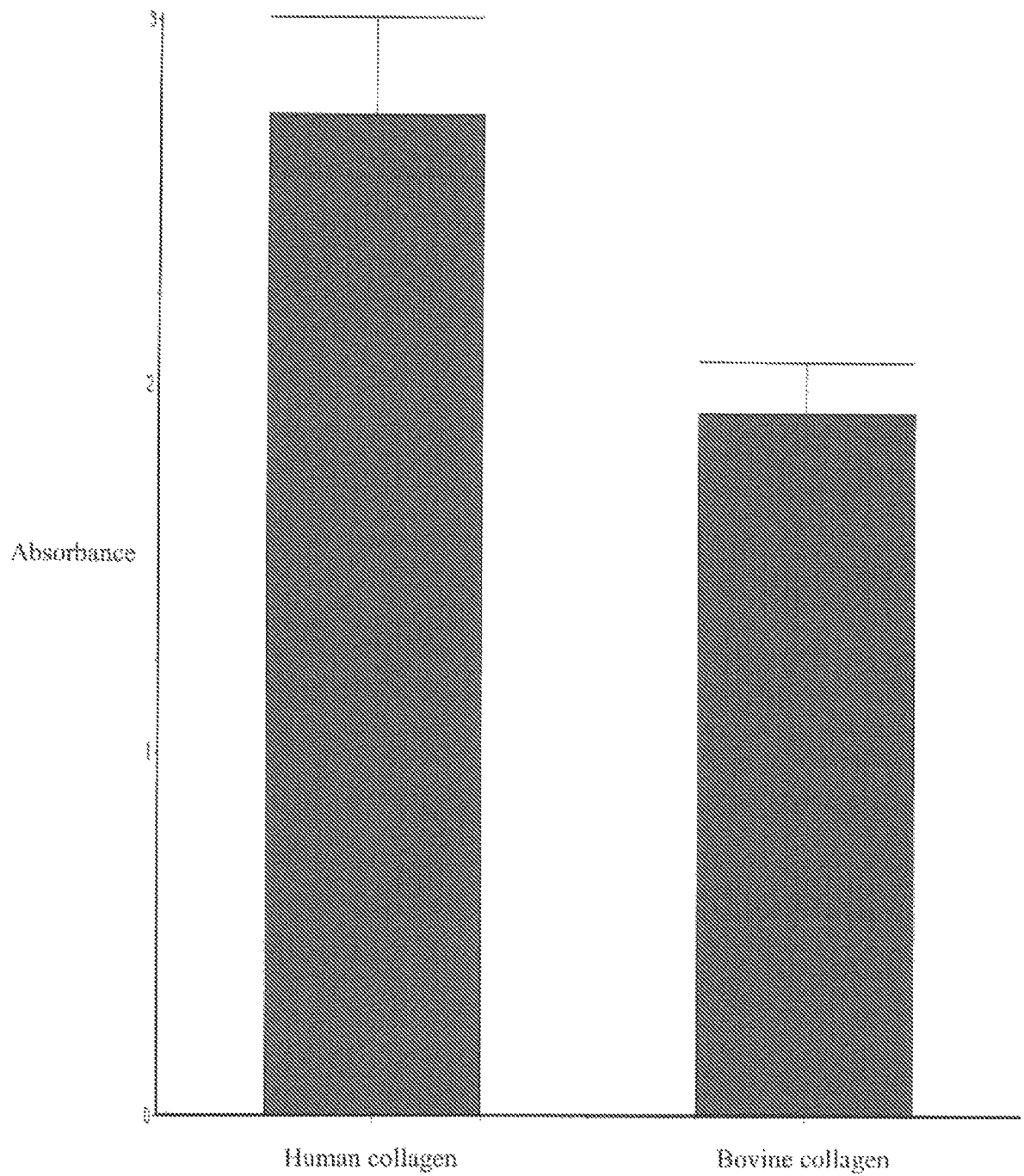
FIG. 2 shows the results of a proliferation assay for mesenchymal stem cells grown on human or bovine collagen membranes.

The results of a proliferation assay for mesenchymal stem cells grown on human or bovine collagen membranes are shown in FIG. 2. An alamar blue assay was used to evaluate the proliferation rate. The higher absorbance for cells grown on human collagen reflects a higher proliferation rate (P value 0.009) relative to cells grown on bovine collagen.

Mesenchymal cells were grown on C2C12 cells were cultured on 1×1 cm 2 in DMEM medium with 10% fetal bovine serum (ATCC) at 5% CO2 for 5 days.

Example 4

Figure 3:
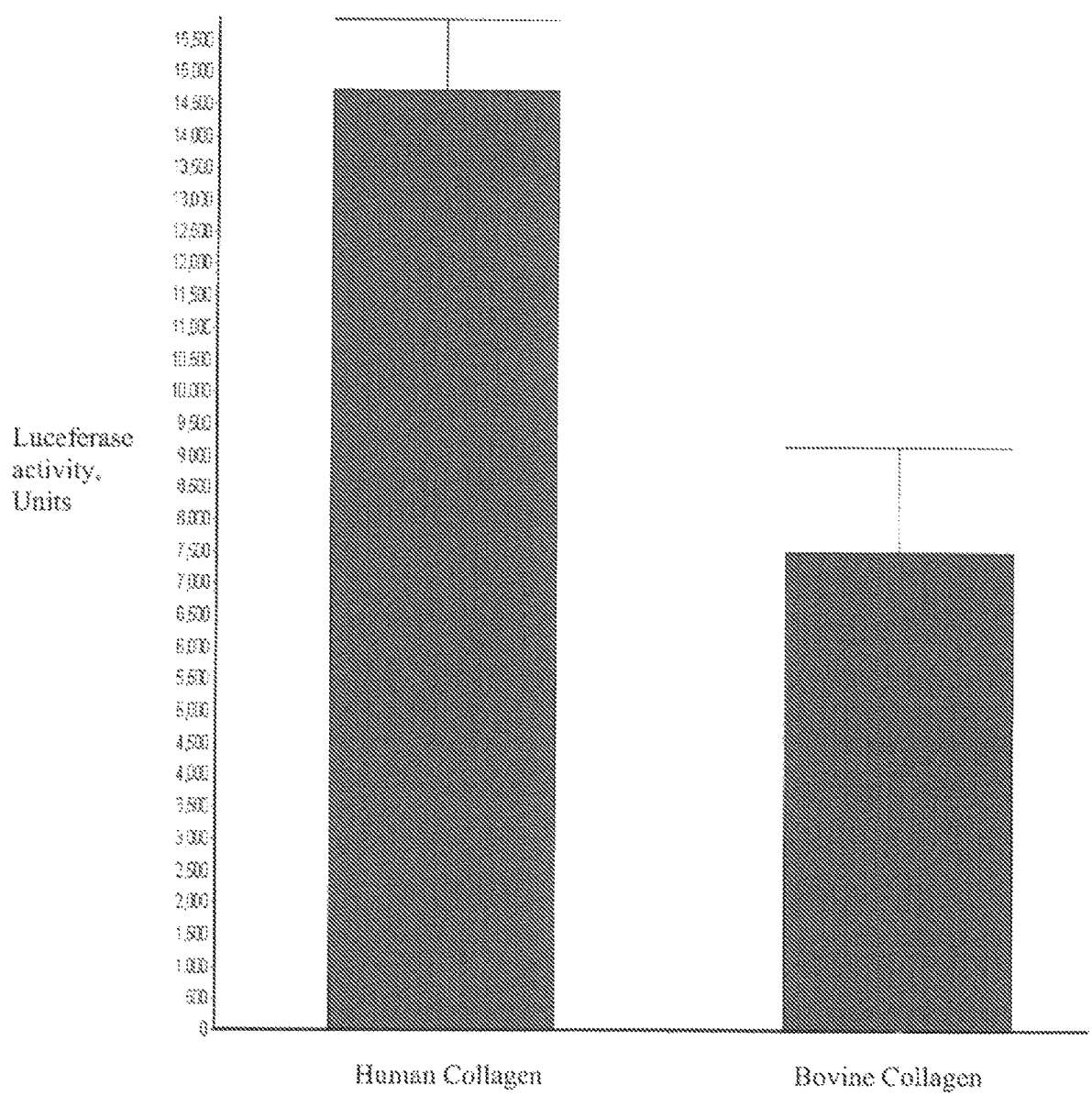
FIG. 3 shows the results of a proliferation assay for human fibroblast cells grown on human or bovine collagen membranes for 24 hours.

The results of a proliferation assay for human fibroblast cells grown on human or bovine collagen membranes for 24 hours are shown in FIG. 3. A luceferase viability assay (Lonza) was used to evaluate the proliferation rate.

The results demonstrate that human fibroblast cells proliferate at a significantly higher rate (P value 0.0016) when grown on a human collagen membrane relative to a bovine collagen membrane.

Example 5

Figure 4:
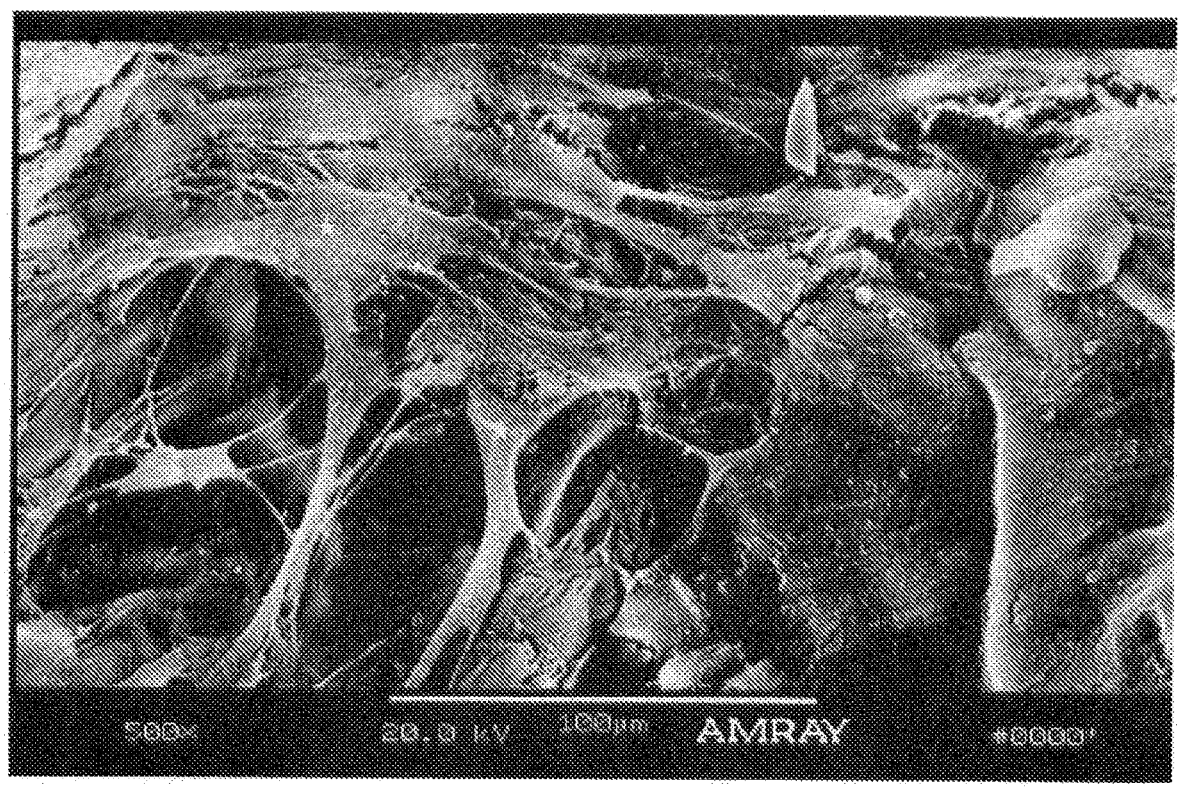
FIG. 4 shows a 500×SEM image of human fibroblasts cultured on human collagen membrane for 3 weeks. The stars indicate the presence of cells.

FIG. 4 is a 500×SEM image of human fibroblasts cultured on human collagen membrane for 3 weeks. The stars indicate the position of fibroblast cells in the image. Fibrils can be seen extending from the cells with a normal morphology for active fibroblast cells. Hence, the human collagen matrix does not adversely affect cellular differentiation.

Example 6

A powdered active collagen matrix is suspended in concentrations of about 1 wt. % to about 99 wt. % in a lubricant fluid in combination with one or more cartilage progenitor cells or cartilage cells, and injected into a joint. For example, cartilage progenitor cells may comprise human mesenchymal stem cells or other cells capable of differentiating to chrondrocytes. The injected material improves lubrication or fluidity of the articulating surfaces of the joint so as to decrease pain or allow more freedom of motion. The active collagen matrix may settle onto the damaged cartilage and begin to function as an active scaffold for tissue repair.

Example 7

An active collagen matrix may be ground to an average particle size of between about 25 µm to about 75 µm, which allows the injection needle size to be reduced to 23 gauge or smaller.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A method of culturing cells, the method comprising:
   (a) forming a matrix sheet comprising an active collagen matrix, wherein the active collagen matrix comprises collagen obtained from a human tissue and growth factors native to human collagen tissue;
   (b) adding rhBMP12 growth factor to the matrix sheet of step (a) such that the resulting amount of total growth factor is from 30% to 50% greater than is found in natural human collagen tissue;
   (c) treating the surface of the matrix sheet of step (b) with a suspension of an activated collagen and letting the suspension dry, wherein the activated collagen suspension is obtained from a human;
   (d) culturing a human mesenchymal stem cell (hMSC) population, obtained from human tissue, on the surface of the treated matrix sheet to induce hMSC differentiation into osteoblasts, chondrocytes, myocytes, fibroblasts, cardiomyocytes, or neurons.

2. The method according to claim 1, wherein step (a) comprises cross-linking the collagen.

3. The method according to claim 1, wherein step (a) comprises cross-linking the collagen.

4. A method of culturing cells, the method comprising:
   (a) forming a matrix sheet comprising an active collagen matrix, wherein the active collagen matrix comprises collagen obtained from a human tissue and growth factors native to human collagen tissue;
   (b) adding rhBMP12 growth factor to the matrix sheet of step (a) such that the resulting amount of total growth factor is from 30% to 50% greater than is found in natural human collagen tissue;
   (c) treating the surface of the matrix sheet of step (b) with a suspension of an activated collagen and letting the suspension dry, wherein the activated collagen suspension is obtained from a human;
   (d) propagating an in vitro human mesenchymal stem cell (hMSC) population, obtained from human tissue, on the surface of the treated matrix sheet to induce hMSC differentiation into osteoblasts, chondrocytes, myocytes, fibroblasts, cardiomyocytes, or neurons.

* * * * *